(12) United States Patent
Zhao et al.

(10) Patent No.: US 9,012,611 B2
(45) Date of Patent: Apr. 21, 2015

(54) USE OF 3,8,12,14, 17,20-OXO-SUBSTITUTED PREGNENE GLYCOSIDES IN THE PREPARATION OF HEALTHCARE PRODUCTS, FOOD ADDITIVES AND PHARMACEUTICALS FOR THE INHIBITION OF APPETITE

(75) Inventors: Weimin Zhao, Shanghai (CN); Shuangzhu Liu, Shanghai (CN); Zhenhua Chen, Shanghai (CN); Luoyi Wang, Shanghai (CN)

(73) Assignee: Institute of Materia Medica, Chinese Academy of Sciences, Shanghai (CN)

( * ) Notice: Subject to any disclaimer, the term of this patent is extended or adjusted under 35 U.S.C. 154(b) by 75 days.

(21) Appl. No.: 13/884,767

(22) PCT Filed: Nov. 7, 2011

(86) PCT No.: PCT/CN2011/001876
§ 371 (c)(1),
(2), (4) Date: Jul. 17, 2013

(87) PCT Pub. No.: WO2012/062042
PCT Pub. Date: May 18, 2012

(65) Prior Publication Data
US 2014/0058074 A1    Feb. 27, 2014

(30) Foreign Application Priority Data
Nov. 11, 2010   (CN) .......................... 2010 1 0540890

(51) Int. Cl.
*C07J 17/00*    (2006.01)
*A61K 31/7034*   (2006.01)

(52) U.S. Cl.
CPC ........... *C07J 17/005* (2013.01); *A61K 31/7034* (2013.01)

(58) Field of Classification Search
CPC ........................ A61K 31/7034; C07J 17/005
USPC ........................................................ 536/5
See application file for complete search history.

(56) References Cited

U.S. PATENT DOCUMENTS 6,376,657 B1 * 4/2002 Van Heerden et al. ........... 536/5

FOREIGN PATENT DOCUMENTS

CN    1660865 A  *  8/2005  ......... A61K 31/7048
CN    16608865       8/2005

OTHER PUBLICATIONS

Hwang et al, J. Nat. Prod. 1999, 62, 640-43.*
Peng et al, Phytomedicine, 2008, 15, 1016-1020.*
International Search Report for PCT/CN2011/001876 mailed Feb. 16, 2012.
B. Wu et al., "Toxicity Research of Cynanchum Auriculatum and Components Thereof", ACTA Medica Sinica, Feb. 1989, 4 (1), pp. 23-25.
J. Chen et al., "Cynauricuosides A, B and C, Steroid Glycosides from the Root of Cynanchum Auriculatum", ACTA Botanica Yunnanica, 1990, 12 (2), pp. 197-210.
N. Yao et al., "Effect of Three $C_{21}$ Steroidal Sapon Ins from Cynanchum Auriculatum on the Inhibition of the Cell Growth and Cell Cycle of Human Lung Cancer A549 Cells", China Journal of Chinese Materia Medics, Jun. 2009, 34 (11), pp. 1418-1421.

* cited by examiner

*Primary Examiner* — Ganapathy Krishnan
(74) *Attorney, Agent, or Firm* — Nixon & Vanderhye P.C.

(57) ABSTRACT

The present invention relates to the use of 3,8,12,14,17,20-oxo-substituted pregnene glycosides having the following formula I in the preparation of healthcare products, food additives and drugs for losing body weight, controlling body weight and inhibiting appetite of human beings or animals, wherein, $R_1$ is a saccharide group, and $R_2$ is an acyl group.

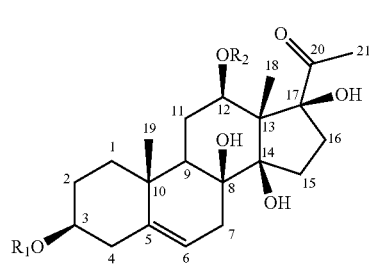

4 Claims, 5 Drawing Sheets

USE OF 3,8,12,14, 17,20-OXO-SUBSTITUTED PREGNENE GLYCOSIDES IN THE PREPARATION OF HEALTHCARE PRODUCTS, FOOD ADDITIVES AND PHARMACEUTICALS FOR THE INHIBITION OF APPETITE

This application in the U.S. national phase of International Application No. PCT/CN2011/001876 filed 7 Nov. 2011 which designated the U.S. and claims priority to CN 201010540890.7 filed 11 Nov. 2010, the entire contents of each of which are hereby incorporated by reference.

TECHNICAL FIELD

The present invention relates to the use of natural 3,8,12,14,17,20-oxo-substituted pregnene glycosides for the inhibition of appetite. In particular, the present invention relates to the use of 3,8,12,14,17,20-oxo-substituted pregnene glycosides in the development of healthcare products, food additives and pharmaceuticals for reducing or controlling body weight and inhibiting appetite of human beings or animals, wherein, the 3,8,12,14,17,20-oxo-substituted pregnene glycosides are separated from medicinal and/or edible *Cynanchum* plant species.

BACKGROUND ART

Obesity means that the adipose tissue in human body is too much for various reasons and goes beyond the average level of normal human being. Obesity may affect the health of organism and is an important factor inducing serious diseases and death. In the whole world, there are over 1.6 billion people who suffer from obesity with different degree. Thus, it is necessary for people suffering from obesity to lose body weight and for people who have obesity tendency to control body weight. The investigation of appetite inhibitors attracts much attention and the marketed drugs mainly include: 1) adrenergic drugs, such as amphetamine and norpseudoephedrine; 2) 5-hydroxytryptamine receptor agonist, such as fenfluramine; 3) monoamine reuptake inhibitor, such as sibutramine; 4) other drugs which can reduce appetite, decrease caloric intake, inhibit the synthesis of adipose, increase the metabolic rate and caloric consumption by the central and peripheral pathways, thus decrease the adipose accumulation. Currently, the commercial appetite inhibitor may change the content and distribution of the chemical substance in brain, but the brain may adapt such condition rapidly, so the body weight will reduce rapidly in short term. However, such drugs may induce serious side effects including hypertension, accelerated heart rate, insomnia, hyperaesthesia and thirsty, and will result in dependence. Therefore, it is significant to develop new natural drugs or health products with high efficiency and low toxicity for losing body weight.

*Cynanchum* is a genus of the Asclepiadaceae family and comprises appropriately 200 plant species which spread in the torrid zone and the temperate zone. In China, there are about 53 *Cynanchum* species which spread in the whole country. Bai Shou Wu is also referred to as Ge Shan Xiao, Bai He Wu, Bai He Shou Wu, Ge Shan Qiao Shandong He Shou Wu, Taishan He Shou Wu, and the like, which originates from *Cynanchum bungei* Decne, *C. auriculatum* Royle ex Wight or *C. wilfordii* Hemsl. of the *Cynanchum* genus in the Asclepiadaceae family. The roots of *Cynanchum auriculatum* have long been used as medicinal and edible plant material with anti-aging effect in Binhai County, Jiangsu Province, China.

Currently, there is no document reporting the use of extract or components of *Cynanchum auriculatum* for inhibiting appetite and in the development of relative product for losing body weight.

DISCLOSURE OF THE INVENTION

The present inventors found from animal test in vivo that, 3,8,12,14,17,20-oxo-substituted pregnene glycosides from *Cynanchum auriculatum*, and a composition thereof have an effect of inhibiting appetite, and such substances can also reduce body weight by decreasing food intake dose.

Thus, one object of the present invention is to provide a use of 3,8,12,14,17,20-oxo-substituted pregnene glycosides having the following formula I in the preparation of healthcare products, food additives and drugs for reducing body weight, controlling body weight and inhibiting appetite of human beings or animals,

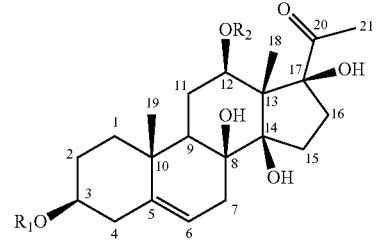

wherein, $R_1$ is a saccharide group, and $R_2$ is an acyl group; the saccharide group is consisted of one or more sugar moieties selected from glucose, cymarose, diginose, mannose, xylose, rhamnose, arabinose and glucuronic acid; and the acyl group is selected from acetyl, cinnamoyl, 3,4-dimethyl-2-amylene acyl, nicotinoyl and benzoyl.

Preferably, the compounds of formula I list as follows:

cynauricuoside A

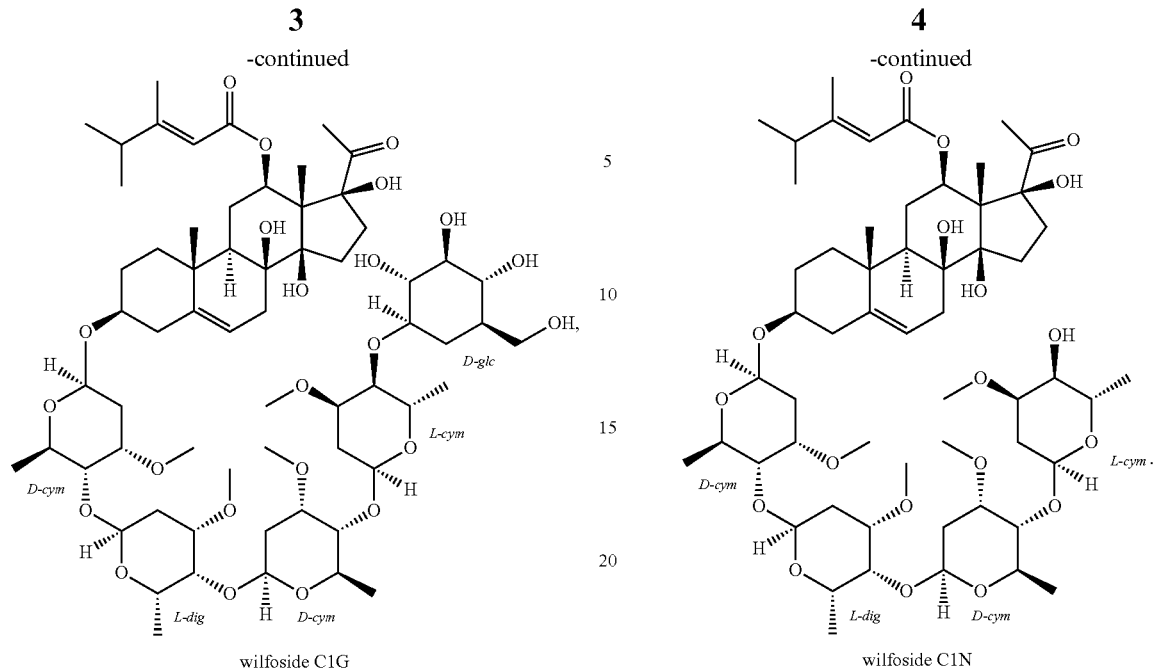

wilfoside C1G

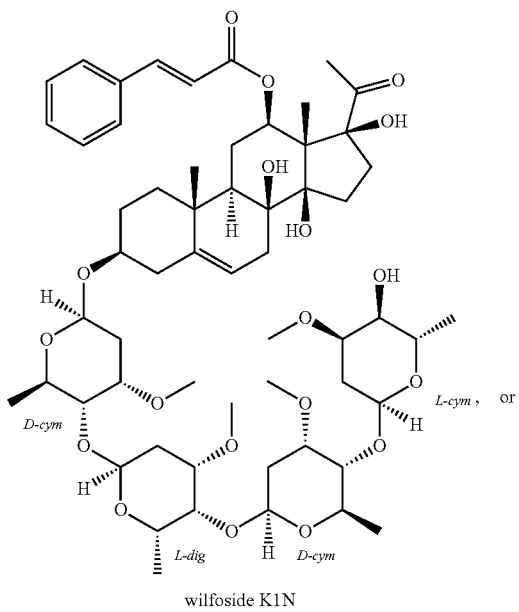

wilfoside K1N wilfoside C1N

The above 3,8,12,14,17,20-oxo-substituted pregnene glycosides may be extracted from the roots of *Cynanchum auriculatum*, a medicinal and edible plant. The roots of *Cynanchum auriculatum* are first sliced and dried, and extracted with 95% ethanol to get a crude extract; then the extract is partitioned between solvents and then separated by column chromatography to get cynauricuoside A, wilfoside C1G, wilfoside C1N and wilfoside K1N.

The above 3,8,12,14,17,20-oxo-substituted pregnene glycosides have an effect of inhibiting appetite, thus can effectively reduce food intake dose and achieve the result of losing body weight.

Another object of the present invention is to provide a composition to prepare healthcare products, food additives and drugs for losing body weight, controlling body weight and inhibiting appetite of human beings or animals, wherein, the composition contains one or more compounds selected from 3,8,12,14,17,20-oxo-substituted pregnene glycosides.

BEST MODE

PREPARATION EXAMPLE

Figure 1:
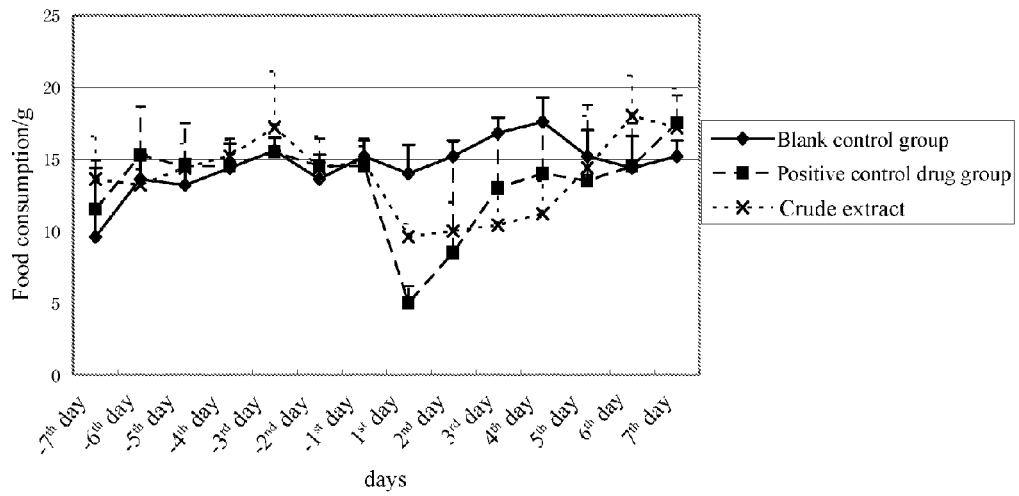
FIG. 1 is a diagram showing that the average food consumption changes with time when the dosage of crude extract containing 3,8,12,14,17,20-oxo-substituted pregnene glycosides of *Cynanchum auriculatum* is 300 mg/kg body weight.

The Preparation of Compounds:
1. Preparation of Pure 3,8,12,14,17,20-oxo-substituted Pregnene Glycosides 10 Kg of fresh roots of *Cynanchum auriculatum* (collected from Binhai County, Jiangsu Province, China) was sliced and dried to get 3 kg of dried substance which was extracted with 95% ethanol under reflux condition for three times. Then the extracts were combined and concentrated under reduced pressure to get an ethanol extract. The extract was mixed with silica gel, and separated by column chromatography over silica gel (200-300 mesh), eluted with a petroleum ether-acetone gradient (3:1 to 2:1), and then with chloroform-methanol (10:1 to 5:1) to get fraction 1 to fraction 6. Fraction 3 was further purified repeatedly by column chromatography over silica gel eluted with petroleum ether-acetone and chloroform-methanol, to obtain pure wilfoside C1N (1.5 g) and wilfoside K1N (2.5 g). Fraction 6 was purified by column chromatography over silica gel eluted with chloroform-methanol to obtain a subfraction (20 g) comprising mainly cynauricuoside A and wilfoside C1G. 2 g sample thereof was weighed and purified by HPLC to obtain pure cynauricuoside A (200 mg) and wilfoside C1G (170 mg).

The structures of the above four 3,8,12,14,17,20-oxo-substituted pregnene glycosides were identified by spectral analysis and by comparison of NMR data with those in the literature. The detailed data are as follows:

Cynauricuoside A: amorphous powder, melting point: 167-173° C.; ESIMS m/z 1271.7 (cation mode, [M+Na]$^+$); 1248.2 (anion mode, [M−H]$^−$); $^1$H-NMR (pyridine-d$_5$, 300 MHz, δ in ppm): 1.36 (3H, s), 1.37, 1.38, 1.44, 1.45 (each 3H, d, J=6.0 Hz), 2.02 (3H, s), 2.49 (3H, s), 3.28 (1H, m), 3.38, 3.39, 3.53, 3.54 (each 3H, s), 4.53 (1H, d, J=7.8 Hz), 4.67 (1H, m), 4.97 (1H, dd, J=10.0, 7.0 Hz), 5.02 (1H, br d, J=3.0 Hz), 5.10 (1H, dd, J=9.0, 3.1 Hz), 5.16 (1H, br d, J=3.0 Hz), 5.24 (1H, br d, J=9.6 Hz), 5.25 (1H, br s), 6.80 (1H, d, J=16.0 Hz), 7.38 (3H), 7.65 (2H), 7.98 (1H, d, J=16.0 Hz); $^{13}$C-NMR (pyridine-d$_5$, 100 MHz) data, please refer to Table 7 (literature: CHEN Jijun, ZHANG Zhuangxin, ZHOU Jun; *Yunnan Plant Research*, 1990, 12(12): 197-210).

Wilfoside C1G: amorphous powder, melting point: 143-147° C., ESIMS m/z 1251.8 (cation mode, [M+Na]$^+$), 1228.2 (anion mode, [M−H]$^−$), $^1$H-NMR (pyridine-d$_5$, 300 MHz, δ in ppm): 0.95, 0.97 (each 3H, d, J=6.5 Hz), 1.35 (3H, s), 1.36, 1.38, 1.41, 1.43 (each 3H, d, J=6.0 Hz), 1.97 (3H, s), 2.17 (3H, s), 2.50 (3H, s), 3.28 (1H, m), 3.41, 3.44, 3.53, 3.54 (each 3H, s), 4.54 (1H, d, J=8.0 Hz), 4.69 (1H, m), 4.95 (1H, dd, J=12.6, 3.0 Hz), 4.99 (1H, br d, J=3.0 Hz), 5.08 (1H, dd, J=9.0, 3.1 Hz), 5.16 (1H, br d, J=3.0 Hz), 5.23 (1H, br d, J=9.0 Hz), 5.29 (1H, br s), 5.85 (1H, br s); $^{13}$C-NMR (pyridine-d$_5$, 100 MHz) data, please refer to Table 7 (literature: CHEN Jijun, ZHANG Zhuangxin, ZHOU Jun; *Yunnan Plant Research*, 1990, 12(12): 197-210).

Wilfoside C1N: amorphous powder, melting point: 140-143° C., ESIMS m/z 1089.7 (cation mode, [M+Na]$^+$), 1066.1 (anion mode, [M−H]$^−$), $^1$H-NMR (pyridine-d$_5$, 300 MHz, δ in ppm): 0.95, 0.97 (each 3H, d, J=6.5 Hz), 1.32 (3H, s), 1.36, 1.37, 1.40, 1.48 (each 3H, d, J=6.0 Hz), 1.96 (3H, s), 2.29 (3H, s), 2.49 (3H, s), 3.26 (1H, m), 3.45, 3.48, 3.52, 3.53 (each 3H, s), 4.48 (1H, m), 4.97 (1H, dd, J=12.6, 3.0 Hz), 5.02 (1H, br d, J=3.0 Hz), 5.09 (1H, dd, J=9.3, 2.1 Hz), 5.15 (1H, br d, J=3.0 Hz), 5.22 (1H, br d, J=9.0 Hz), 5.30 (1H, br s), 5.84 (1H, br s);

$^{13}$C-NMR (pyridine-d$_5$, 100 MHz) data, please refer to Table 7 (literature: CHEN Jijun, ZHANG Zhuangxin, ZHOU Jun; *Yunnan Plant Research*, 1990, 12(12): 197-210).

Wilfoside K1N: amorphous powder, melting point: 183-187° C., ESIMS m/z 1109.7 (cation mode, [M+Na]$^+$), 1086.1 (anion mode, [M−H]$^−$), $^1$H-NMR (pyridine-d$_5$, 300 MHz, δ in ppm): 1.36 (3H, s), 1.37, 1.38, 1.42, 1.49 (each 3H, d, J=6.0 Hz), 2.02 (3H, s), 2.54 (3H, s), 3.27 (1H, m), 3.42, 3.44, 3.53, 3.54 (each 3H, s), 4.97 (1H, dd, J=9.8, 6.0 Hz), 4.97 (1H, m), 4.98 (1H, br d, J=3.0 Hz), 5.09 (1H, dd, J=8.0, 2.1 Hz), 5.15 (1H, br d, J=3.0 Hz), 5.23 (1H, br d, J=9.0 Hz), 5.32 (1H, br s), 6.81 (1H, d, J=16.0 Hz), 7.38 (3H), 7.65 (2H), 7.99 (1H, d, J=16.0 Hz); $^{13}$C-NMR (pyridine-d$_5$, 100 MHz) data, please refer to Table 7 (literature: CHEN Jijun, ZHANG Zhuangxin, ZHOU Jun; *Yunnan Plant Research*, 1990, 12(12): 197-210).

2. Preparation of Extract Rich in 3,8,12,14,17,20-oxo-substituted Pregnene Glycosides 1.0 kg of dried roots of *Cynanchum auriculatum* (collected from Binhai County, Jiangsu Province, China) was powdered and extracted with ethyl acetate under reflux condition for three times. The extracts were combined and concentrated under reduced pressure. Then the concentrate was extracted with warm petroleum ether to remove the lipid. The insoluble substances were collected and dried to obtain light yellow powder (15 g). After analyzed by TLC, HPLC-ELSD and HPLC-MS and compared with authentic samples of cynauricuoside A, wilfoside C1G, wilfoside C1N and wilfoside K1N, the above mentioned light yellow powder was mainly comprised of 3,8,12,14,17,20-oxo-substituted pregnene glycosides.

EXPERIMENTAL EXAMPLES

Animal Test in vivo:

6-7 weeks-old female Wistar rat (purchased from Shanghai Laboratory Animal Center of Chinese Academy of Sciences) (weight: 110-150 g) was raised alone in suspended metal cage. After the experimental rat was obtained, it was checked to make sure whether they were abnormal or had obvious disease signs. The rat can freely obtain the drinking-water and feed for rodent (RM1(E)AQC). The feeding cage was controlled to receive 12 h illumination (from 07:00 to 19:00) and to be in a dark environment for 12 h, and the room temperature and relative humidity were controlled to be 21±3° C. and 55±15% respectively and not to deviate the upper and lower limit. The rats were randomly divided into groups depending on the body weight according to random number table to make the average weight in each group are approximately equal. Before the test, the rats were pre-trained suitably for one week (from −7$^{th}$ day to −1$^{st}$ day) during which the consumptions of feed and drinking water were recorded.

Each group of drug to be tested, positive control group, and blank control group consisted of 5 rats, respectively. The tested drug and positive control drug were mixed with wheaten starch before the administration and formulated to suspension with required doses according to 10 mL/kg of administration volume. The positive control drug was sibutramine hydrochloride and the administration dosage was 15 mg/kg body weight. In the blank control group, only equal amount of starch was used to formulate suspension for administration by injection in a same volume. The administration time is the $1^{st}$ day, $2^{nd}$ day and $3^{rd}$ day. The body weight of the rat, the consumption of the feed (the weight of the feeding hopper) and consumption of the drinking water (bottle weight) were recorded from the $-7^{th}$ day to the $7^{th}$ day.

Experimental Example 1

Figure 2:
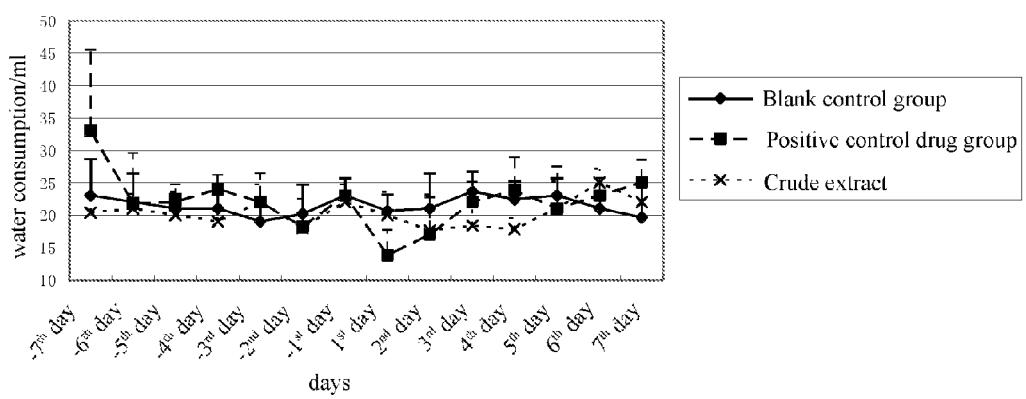
FIG. 2 is a diagram showing that the average water consumption changes with time when the dosage of crude extract containing 3,8,12,14,17,20-oxo-substituted pregnene glycosides of *Cynanchum auriculatum* is 300 mg/kg body weight.
Figure 3:
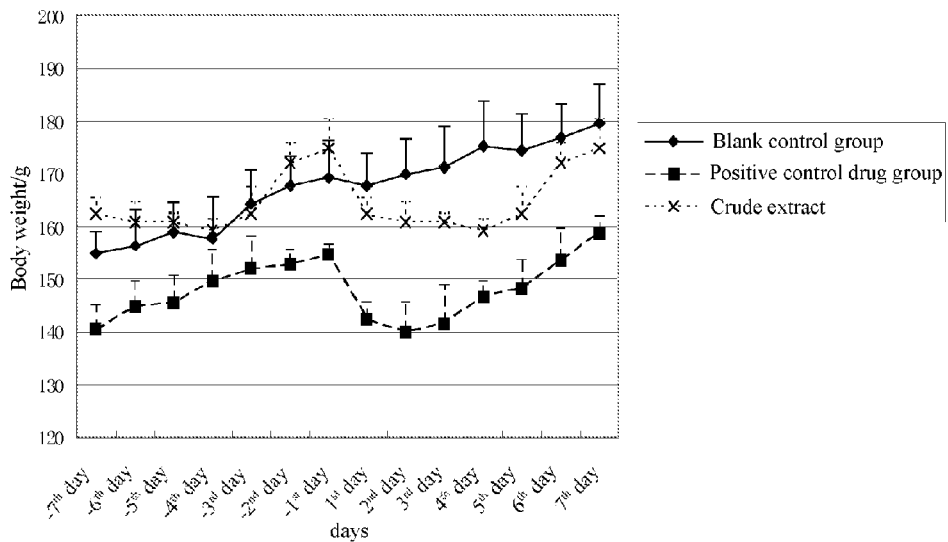
FIG. 3 is a diagram showing that the average body weight changes with time when the dosage of crude extract containing 3,8,12,14,17,20-oxo-substituted pregnene glycosides of *Cynanchum auriculatum* is 300 mg/kg body weight.

For the crude extract rich in 3,8,12,14,17,20-oxo-substituted pregnene glycosides, the animal test was carried out according to the test method recorded in this application, in which the administration dosage of the crude extract is 300 mg/kg and the administration dosage of the positive control drug sibutramine hydrochloride is 15 mg/kg. The experimental data were shown in Table 1 to Table 3. From FIG. 1 to FIG. 3, it can be found that, during the administration of the drugs, the average food consumptions in the group with the administration of the crude extract rich in 3,8,12,14,17,20-oxo-substituted pregnene glycosides were greatly different from those in the blank control group, there was not so much different in water consumption doses therebetween, and the body weight in the group with the administration of the crude extract rich in 3,8,12,14,17,20-oxo-substituted pregnene glycosides decreased and the decreasing tendency fitted well to that in the positive control drug group.

Experimental Example 2

Figure 4:
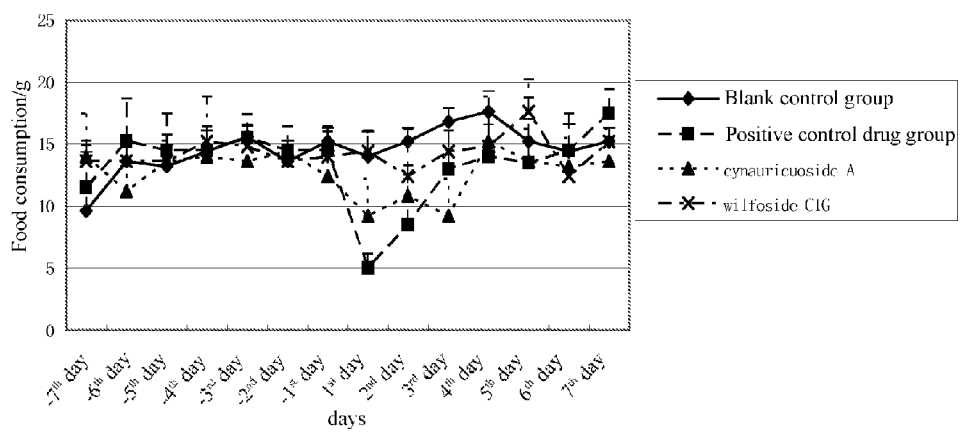
FIG. 4 is a diagram showing that the average food consumption changes with time when the dosages of cynauricuoside A and wilfoside C1G are 50 mg/kg body weight, respectively.
Figure 5:
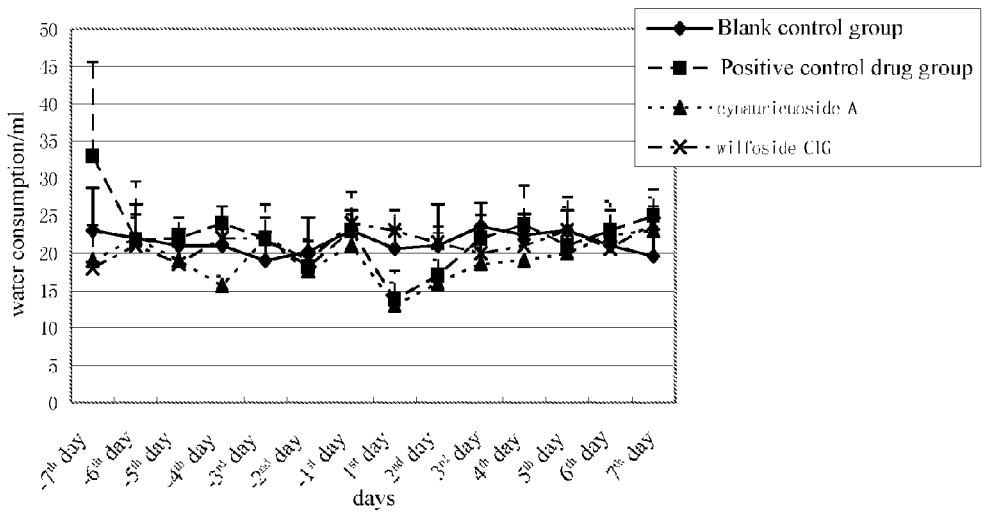
FIG. 5 is a diagram showing that the average water consumption changes with time when the dosages of cynauricuoside A and wilfoside C1G are 50 mg/kg body weight, respectively.
Figure 6:
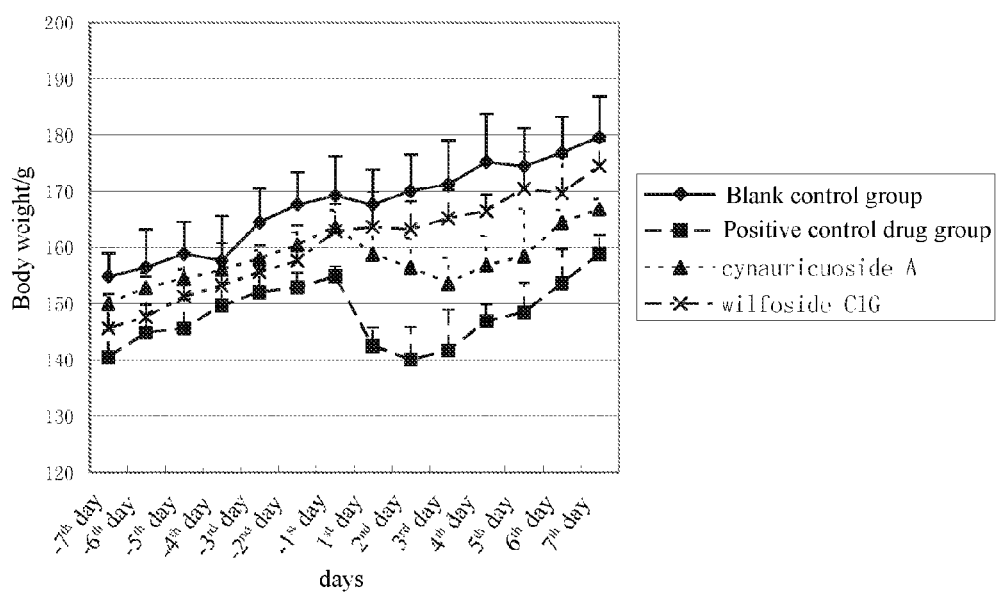
FIG. 6 is a diagram showing that the average body weight changes with time when the dosages of cynauricuoside A and wilfoside C1G are 50 mg/kg body weight, respectively.

The animal test of cynauricuoside A was carried out according to the test method recorded in this application, in which the administration dosage of the cynauricuoside A is 50 mg/kg and the administration dosage of positive control drug sibutramine hydrochloride is 15 mg/kg. The experimental data were shown in Table 1 to Table 3. From FIG. 4 to FIG. 6, it can be seen that, during the administration of the drugs, the average food consumptions in cynauricuoside A group were greatly less than those in the blank control group, there were no much differences in water consumption doses therebetween, and the tendency of body weight change was greatly different, it relatively fitted the decreasing tendency of the average body weight in the positive control drug group.

Experimental Example 3

The animal test of wilfoside C1G was carried out according to the test method recorded in this application, in which the administration dosage of the wilfoside C1G is 50 mg/kg and the administration dosage of the positive control drug sibutramine hydrochloride is 15 mg/kg. The experimental data were shown in Table 1 to Table 3. From FIG. 4 to FIG. 6, it can be seen that although, during the administration of drugs, there were no great differences between the average food consumptions in wilfoside C1G group and that in the blank control group, the water consumption doses and the body weight therebetween, the reduction tendency in the average food consumptions and the average body weight still existed.

Experimental Example 4

Figure 7:
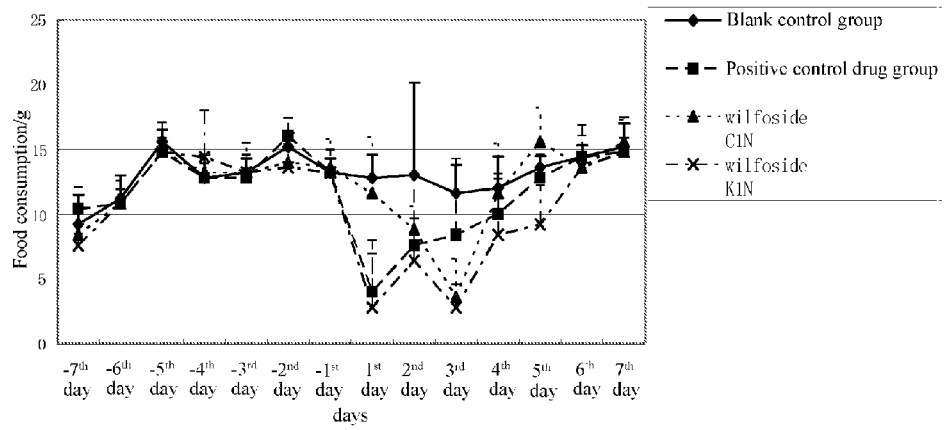
FIG. 7 is a diagram showing that the average food consumption changes with time when the dosages of wilfoside C1N and wilfoside K1N are 50 mg/kg body weight, respectively.
Figure 8:
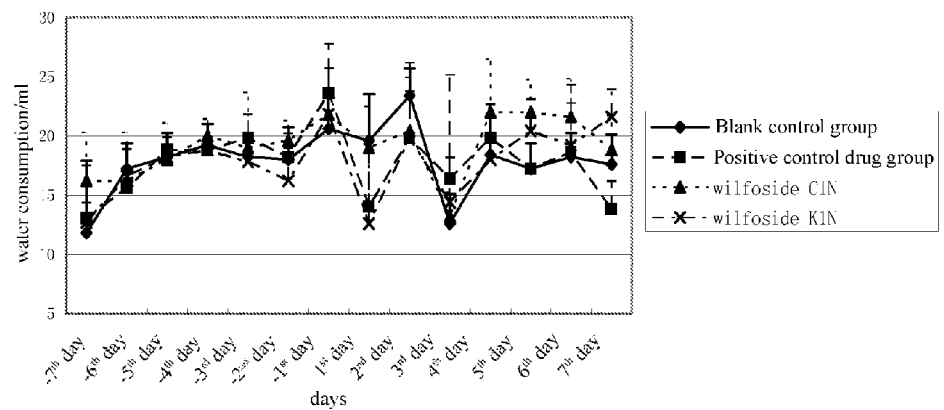
FIG. 8 is a diagram showing that the average water consumption changes with time when the dosages of wilfoside C1N and wilfoside K1N are 50 mg/kg body weight, respectively.
Figure 9:
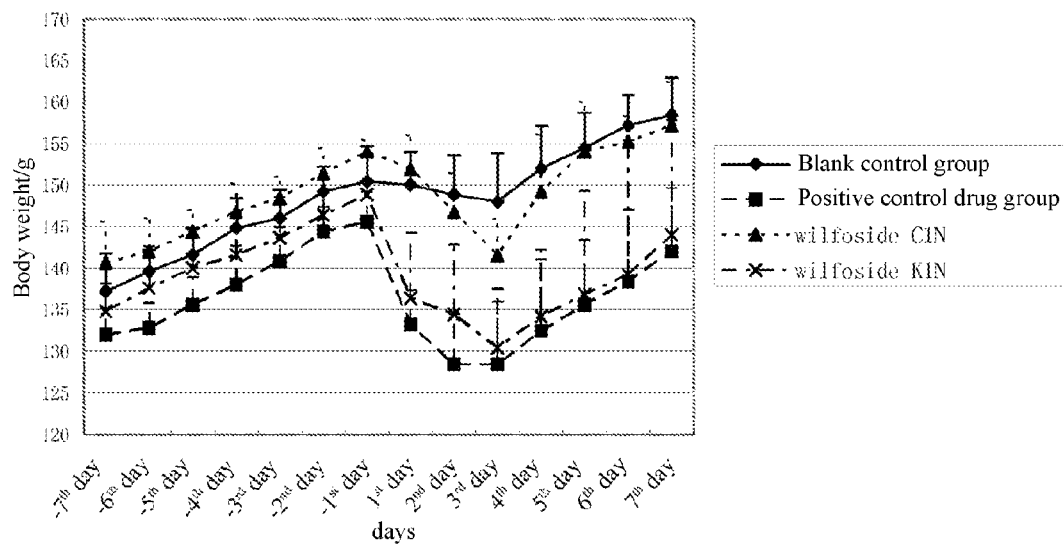
FIG. 9 is a diagram showing that the average body weight changes with time when the dosages of wilfoside C1N and wilfoside K1N are 50 mg/kg body weight, respectively.

The animal test of wilfoside C1N was carried out according to the test method recorded in this application, in which the administration dosage of the wilfoside C1N is 50 mg/kg and the administration dosage of the positive control drug sibutramine hydrochloride is 15 mg/kg. The experimental data were shown in Table 4 to Table 6. From FIG. 7 to FIG. 9, it can be seen that, during the administration of drugs, the average food consumptions in wilfoside C1N group were greatly different from those in the blank group, there were no much differences in the water consumption doses therebetween, and although there were no great differences in the body weights therebetween, the decreasing tendency thereof still existed and relatively fitted that in the positive control drug group.

Experimental Example 5

The animal test of wilfoside K1N was carried out according to the test method recorded in this application, in which the administration dosage of the wilfoside K1N is 50 mg/kg and the administration dosage of positive control drug sibutramine hydrochloride is 15 mg/kg. The experimental data were shown in Table 4 to Table 6. From FIG. 7 to FIG. 9, it can be seen that, during the administration of drugs, the average food consumptions, the average of water consumptions and the average body weights in wilfoside K1N group were greatly different from those in the blank group, and the decreasing tendency of the average body weights in wilfoside K1N group fitted that in the positive control drug group well.

Through the described animal test in vivo, the present inventors found that the 3,8,12,14,17,20-oxo-substituted pregnene glycosides have an effect of inhibiting appetite, and thus can achieve the object of losing body weight by reducing food intake dose.

TABLE 1

Average food consumptions before and after the administration of drugs (unit: g)

| Groups | $-7^{th}$ day | $-6^{th}$ day | $-5^{th}$ day | $-4^{th}$ day | $-3^{rd}$ day | $-2^{nd}$ day | $-1^{st}$ day | $1^{st}$ day | $2^{nd}$ day | $3^{rd}$ day | $4^{th}$ day | $5^{th}$ day | $6^{th}$ day | $7^{th}$ day |
|---|---|---|---|---|---|---|---|---|---|---|---|---|---|---|
| Blank control group | 9.6 ± 4.77 | 13.6 ± 1.67 | 13.2 ± 1.79 | 14.4 ± 1.67 | 15.6 ± 0.89 | 13.6 ± 1.67 | 15.2 ± 1.10 | 14 ± 2.00 | 15.2 ± 1.10 | 16.8 ± 1.10 | 17.6 ± 1.67 | 15.2 ± 1.79 | 14.4 ± 2.19 | 15.2 ± 1.10 |
| Positive control group 15 mg/kg | 11.5 ± 3.42 | 15.3 ± 3.40 | 14.5 ± 3.00 | 14.5 ± 1.91 | 15.5 ± 1.91 | 14.5 ± 1.91 | 14.5 ± 1.91 | 5.0 ± 1.15 | 8.5 ± 7.72 | 13.0 ± 3.83 | 14.0 ± 3.65 | 13.5 ± 5.26 | 14.5 ± 3.00 | 17.5 ± 1.91 |
| Crude extract 300 mg/kg | 13.6 ± 2.79 | 13.2 ± 1.10 | 14.4 ± 1.67 | 15.2 ± 1.10 | 17.2 ± 3.90 | 14.4 ± 2.19 | 14.8 ± 1.10 | 9.6 ± 0.89 | 10 ± 2.00 | 10.4 ± 2.19 | 11.2 ± 2.28 | 14.4 ± 3.58 | 18 ± 2.83 | 17.2 ± 2.68 |
| Cynauricuoside A 50 mg/kg | 14 ± 3.46 | 11.2 ± 4.15 | 13.6 ± 1.67 | 14 ± 1.41 | 13.6 ± 1.67 | 14.4 ± 0.89 | 12.4 ± 1.67 | 9.2 ± 3.03 | 10.8 ± 1.79 | 9.2 ± 3.03 | 15.2 ± 3.63 | 13.6 ± 2.61 | 13.2 ± 2.28 | 13.6 ± 2.61 |

TABLE 1-continued

Average food consumptions before and after the administration of drugs (unit: g)

| Groups | −7th day | −6th day | −5th day | −4th day | −3rd day | −2nd day | −1st day | 1st day | 2nd day | 3rd day | 4th day | 5th day | 6th day | 7th day |
|---|---|---|---|---|---|---|---|---|---|---|---|---|---|---|
| Wilfoside C1G 50 mg/kg | 13.6 ± 1.67 | 13.6 ± 1.67 | 13.6 ± 2.19 | 15.2 ± 3.63 | 14.8 ± 1.79 | 13.6 ± 1.67 | 14 ± 2.00 | 14.4 ± 1.67 | 12.4 ± 0.89 | 14.4 ± 1.67 | 14.8 ± 1.79 | 17.6 ± 2.61 | 12.4 ± 2.19 | 15.2 ± 1.10 |

TABLE 2

Average water consumptions before and after the administration of drugs (unit: mL)

| Groups | −7th day | −6th day | −5th day | −4th day | −3rd day | −2nd day | −1st day | 1st day | 2nd day | 3rd day | 4th day | 5th day | 6th day | 7th day |
|---|---|---|---|---|---|---|---|---|---|---|---|---|---|---|
| Blank control group | 23 ± 5.70 | 22 ± 4.47 | 21 ± 2.24 | 21 ± 2.24 | 19 ± 2.24 | 20.2 ± 4.55 | 23 ± 2.74 | 20.6 ± 2.61 | 21 ± 5.48 | 23.6 ± 3.13 | 22.4 ± 2.88 | 23 ± 2.74 | 21 ± 2.24 | 19.6 ± 5.08 |
| Positive control group 15 mg/kg | 33 ± 12.55 | 21.8 ± 7.82 | 22 ± 2.74 | 24 ± 2.24 | 22 ± 4.47 | 18.2 ± 2.05 | 23 ± 2.74 | 13.8 ± 3.90 | 17 ± 5.70 | 22 ± 3.08 | 23.8 ± 5.22 | 21 ± 6.52 | 23 ± 2.74 | 25 ± 3.54 |
| Crude extract 300 mg/kg | 20.4 ± 2.88 | 21 ± 2.24 | 20 ± 3.54 | 19 ± 4.18 | 22 ± 2.74 | 18 ± 4.47 | 22 ± 2.74 | 20 ± 3.54 | 17.6 ± 5.59 | 18.4 ± 3.21 | 17.8 ± 1.79 | 21 ± 4.18 | 25 ± 2.12 | 22 ± 3.46 |
| Cynauricuoside A 50 mg/kg | 19 ± 4.18 | 22 ± 2.74 | 19 ± 2.24 | 15.6 ± 1.34 | 22 ± 4.47 | 17.6 ± 4.34 | 21 ± 4.18 | 13 ± 3.08 | 16 ± 3.08 | 18.6 ± 2.19 | 19 ± 4.18 | 20 ± 6.12 | 22.4 ± 4.56 | 23 ± 4.47 |
| Wilfoside C1G 50 mg/kg | 18 ± 5.70 | 21 ± 4.18 | 18.6 ± 2.19 | 22 ± 2.74 | 22 ± 2.74 | 19 ± 2.65 | 24 ± 4.18 | 23 ± 2.74 | 21.4 ± 2.19 | 20 ± 1.41 | 21 ± 4.18 | 23 ± 4.47 | 20.6 ± 2.61 | 24 ± 2.24 |

TABLE 3

Average body weight before and after the administration of drugs (unit: g)

| Groups | −7th day | −6th day | −5th day | −4th day | −3rd day | −2nd day | −1st day | 1st day | 2nd day | 3rd day | 4th day | 5th day | 6th day | 7th day |
|---|---|---|---|---|---|---|---|---|---|---|---|---|---|---|
| Blank control group | 154.8 ± 4.15 | 156.4 ± 6.84 | 158.8 ± 5.76 | 157.6 ± 7.92 | 164.4 ± 6.07 | 167.6 ± 5.73 | 169.2 ± 7.01 | 167.6 ± 6.23 | 170 ± 6.48 | 171.2 ± 7.82 | 175.2 ± 8.56 | 174.4 ± 6.84 | 176.8 ± 6.42 | 179.6 ± 7.27 |
| Positive control group 15 mg/kg | 140.4 ± 4.77 | 144.8 ± 5.02 | 145.6 ± 5.18 | 149.6 ± 6.07 | 152 ± 6.16 | 152.8 ± 2.68 | 154.8 ± 1.79 | 142.4 ± 3.29 | 140 ± 5.83 | 141.6 ± 7.27 | 146.8 ± 3.03 | 148.4 ± 5.18 | 153.6 ± 6.07 | 158.8 ± 3.35 |
| Crude extract 300 mg/kg | 162.4 ± 2.97 | 160.8 ± 3.90 | 160.8 ± 1.79 | 159.2 ± 2.28 | 162.4 ± 5.18 | 172 ± 4.00 | 174.8 ± 5.59 | 162.4 ± 2.97 | 160.8 ± 3.90 | 160.8 ± 1.79 | 159.2 ± 2.28 | 162.4 ± 5.18 | 172 ± 4.00 | 174.8 ± 5.59 |
| cynauricuoside A 50 mg/kg | 150 ± 1.41 | 152.8 ± 2.68 | 154.4 ± 1.67 | 156 ± 1.41 | 158 ± 1.41 | 160.4 ± 2.19 | 163.6 ± 2.97 | 158.8 ± 5.59 | 156.4 ± 5.18 | 153.6 ± 4.56 | 156.8 ± 5.22 | 158.4 ± 8.41 | 164.4 ± 2.19 | 166.8 ± 1.79 |
| Wilfoside C1G 50 mg/kg | 145.6 ± 6.07 | 147.6 ± 7.13 | 151.2 ± 7.29 | 153.2 ± 7.56 | 155.6 ± 4.77 | 157.6 ± 6.23 | 162.8 ± 4.82 | 163.6 ± 6.23 | 163.2 ± 5.02 | 165.2 ± 5.02 | 166.4 ± 2.97 | 170.4 ± 6.54 | 169.6 ± 6.54 | 174.4 ± 4.56 |

TABLE 4

Average food consumptions before and after the administration of drugs (unit: g)

| Groups | −7th day | −6th day | −5th day | −4th day | −3rd day | −2nd day | −1st day | 1st day | 2nd day | 3rd day | 4th day | 5th day | 6th day | 7th day |
|---|---|---|---|---|---|---|---|---|---|---|---|---|---|---|
| Blank control group | 9.2 ± 2.28 | 11.2 ± 1.79 | 15.6 ± 0.89 | 12.8 ± 1.79 | 13.2 ± 1.10 | 15.2 ± 1.10 | 13.2 ± 1.10 | 12.8 ± 1.79 | 13 ± 7.14 | 11.6 ± 2.19 | 12 ± 2.45 | 13.6 ± 0.89 | 14.4 ± 0.89 | 15.2 ± 1.79 |

TABLE 4-continued

Average food consumptions before and after the administration of drugs (unit: g)

| Groups | −7th day | −6th day | −5th day | −4th day | −3rd day | −2nd day | −1st day | 1st day | 2nd day | 3rd day | 4th day | 5th day | 6th day | 7th day |
|---|---|---|---|---|---|---|---|---|---|---|---|---|---|---|
| Positive control group 15 mg/kg | 10.4 ± 1.67 | 10.8 ± 1.10 | 14.8 ± 2.28 | 12.8 ± 1.10 | 12.8 ± 1.79 | 16 ± 1.41 | 13.2 ± 1.10 | 4 ± 4.00 | 7.6 ± 5.55 | 8.4 ± 5.90 | 10 ± 3.16 | 12.8 ± 1.79 | 14.4 ± 1.67 | 14.8 ± 1.10 |
| Wilfoside C1N 50 mg/kg | 8.4 ± 0.89 | 10.8 ± 1.79 | 14.8 ± 2.28 | 13.2 ± 1.10 | 13.2 ± 1.10 | 14 ± 1.41 | 13.6 ± 2.19 | 11.6 ± 4.34 | 8.8 ± 1.79 | 3.6 ± 2.97 | 11.6 ± 3.85 | 15.6 ± 2.61 | 13.6 ± 1.67 | 15.6 ± 1.67 |
| Wilfoside K1N 50 mg/kg | 7.6 ± 0.89 | 10.8 ± 1.10 | 14.8 ± 1.10 | 14.4 ± 3.58 | 13.2 ± 2.28 | 13.6 ± 1.67 | 13.2 ± 1.79 | 2.8 ± 4.15 | 6.4 ± 3.29 | 2.8 ± 1.79 | 8.4 ± 4.34 | 9.2 ± 3.03 | 13.6 ± 3.29 | 14.8 ± 2.68 |

TABLE 5

Average water consumptions before and after the administration of drugs (unit: mL)

| Groups | −7th day | −6th day | −5th day | −4th day | −3rd day | −2nd day | −1st day | 1st day | 2nd day | 3rd day | 4th day | 5th day | 6th day | 7th day |
|---|---|---|---|---|---|---|---|---|---|---|---|---|---|---|
| Blank control group | 11.8 ± 6.06 | 17.2 ± 2.17 | 18.2 ± 2.05 | 19.2 ± 1.79 | 18.2 ± 2.05 | 18 ± 2.74 | 20.6 ± 2.61 | 19.6 ± 3.91 | 23.4 ± 2.30 | 12.6 ± 2.51 | 18.4 ± 3.21 | 17.2 ± 2.17 | 18.2 ± 2.05 | 17.6 ± 2.51 |
| Positive control group 15 mg/kg | 13 ± 4.47 | 15.6 ± 1.34 | 18.8 ± 1.10 | 18.8 ± 1.10 | 19.8 ± 2.05 | 18.2 ± 2.05 | 23.6 ± 4.16 | 14 ± 5.48 | 19.8 ± 6.38 | 16.4 ± 8.79 | 19.8 ± 2.86 | 17.2 ± 2.17 | 18.6 ± 4.16 | 13.8 ± 2.39 |
| wilfoside C1N 50 mg/kg | 16.2 ± 4.09 | 16.2 ± 4.09 | 18 ± 3.08 | 20 ± 1.41 | 19 ± 4.69 | 19.6 ± 1.67 | 21.8 ± 2.17 | 19 ± 3.46 | 20.4 ± 4.56 | 13.2 ± 2.05 | 22 ± 4.47 | 22 ± 2.74 | 21.6 ± 3.21 | 18.8 ± 2.95 |
| wilfoside K1N 50 mg/kg | 12.7 ± 1.64 | 16.6 ± 2.30 | 18.2 ± 2.05 | 18.8 ± 1.10 | 17.8 ± 2.28 | 16.2 ± 2.77 | 21.8 ± 3.90 | 12.6 ± 6.15 | 19.8 ± 3.96 | 14.4 ± 3.78 | 18 ± 2.12 | 20.4 ± 2.70 | 19.2 ± 5.12 | 21.6 ± 2.30 |

TABLE 6

Average body weight before and after the administration of drugs (unit: g)

| Groups | −7th day | −6th day | −5th day | −4th day | −3rd day | −2nd day | −1st day | 1st day | 2nd day | 3rd day | 4th day | 5th day | 6th day | 7th day |
|---|---|---|---|---|---|---|---|---|---|---|---|---|---|---|
| Blank control group | 137.2 ± 4.60 | 139.6 ± 2.61 | 141.6 ± 3.29 | 144.8 ± 3.63 | 146 ± 3.46 | 149.2 ± 3.03 | 150.4 ± 4.34 | 150 ± 4.00 | 148.8 ± 4.82 | 148 ± 5.83 | 152 ± 5.10 | 154.4 ± 4.34 | 157.2 ± 3.63 | 158.4 ± 4.56 |
| Positive control group 15 mg/kg | 132 ± 3.16 | 132.8 ± 3.03 | 135.6 ± 3.29 | 138 ± 4.69 | 140.8 ± 4.15 | 144.4 ± 2.97 | 145.6 ± 3.58 | 133.2 ± 4.15 | 128.4 ± 6.07 | 128.4 ± 9.10 | 132.4 ± 8.65 | 135.6 ± 7.80 | 138.4 ± 8.65 | 142 ± 7.62 |
| Wilfoside C1N 50 mg/kg | 140.6 ± 4.98 | 142 ± 4.00 | 144.4 ± 2.61 | 146.8 ± 3.35 | 148.4 ± 2.61 | 151.4 ± 2.97 | 154 ± 1.41 | 152 ± 4.00 | 146.8 ± 4.60 | 141.6 ± 4.34 | 149.2 ± 6.87 | 154 ± 6.00 | 155.2 ± 3.03 | 157.2 ± 5.22 |
| Wilfoside K1N 50 mg/kg | 134.8 ± 3.35 | 137.6 ± 4.98 | 140 ± 4.69 | 141.6 ± 4.98 | 143.6 ± 4.98 | 146.4 ± 4.56 | 148.8 ± 5.76 | 136.4 ± 7.80 | 134.4 ± 8.41 | 130.4 ± 5.55 | 134.2 ± 8.01 | 136.8 ± 12.54 | 139.2 ± 16.16 | 144 ± 13.78 |

TABLE 7

13C-NMR data of compounds cynauricuoside A, wilfoside K1N, wilfoside C1G and wilfoside C1N (pyridine-d5, 100 MHz)

| | Aglycone | | | | | Saccharide group | | | |
|---|---|---|---|---|---|---|---|---|---|
| | cynauricuoside A | wilfoside K1N | wilfoside C1G | wilfoside C1N | | cynauricuoside A | wilfoside K1N | wilfoside C1G | wilfoside C1N |
| 1 | 39.2 | 39.2 | 39.2 | 39.2 | D-cym (connect with C-3) 1 | 96.1 | 96.1 | 96.1 | 96.1 |
| 2 | 29.9 | 29.9 | 29.9 | 29.9 | 2 | 35.4 | 35.3 | 35.3 | 35.3 |
| 3 | 77.7 | 77.6 | 77.6 | 77.6 | 3 | 77.5 | 77.6 | 77.5 | 77.5 |
| 4 | 38.9 | 38.9 | 38.9 | 38.9 | 4 | 82.5 | 82.4 | 82.4 | 82.4 |
| 5 | 139.3 | 139.3 | 139.3 | 139.3 | 5 | 69.2 | 69.2 | 69.2 | 69.2 |
| 6 | 119.2 | 119.2 | 119.2 | 119.2 | 6 | 18.7 | 18.7 | 18.7 | 18.7 |
| 7 | 33.8 | 33.8 | 33.8 | 33.8 | OMe | 57.2 | 57.3 | 57.2 | 57.2 |
| 8 | 74.3 | 74.5 | 74.2 | 74.2 | L-dig 1 | 100.9 | 100.9 | 100.9 | 100.9 |
| 9 | 44.5 | 44.5 | 44.5 | 44.5 | 2 | 32.5 | 32.5 | 32.5 | 32.5 |
| 10 | 37.4 | 37.4 | 37.4 | 37.4 | 3 | 73.8 | 73.8 | 73.8 | 73.8 |
| 11 | 25.0 | 25.0 | 25.0 | 25.0 | 4 | 74.5 | 74.6 | 74.5 | 74.6 |
| 12 | 73.6 | 73.6 | 72.5 | 72.5 | 5 | 67.4 | 67.4 | 67.4 | 67.4 |
| 13 | 58.1 | 58.1 | 57.9 | 57.9 | 6 | 17.8 | 17.9 | 17.8 | 17.9 |
| 14 | 89.5 | 89.5 | 89.4 | 89.4 | OMe | 55.3 | 55.3 | 55.3 | 55.3 |
| 15 | 34.7 | 34.7 | 34.8 | 34.8 | D-cym (in the middle of the accharide chain) 1 | 99.4 | 99.4 | 99.4 | 99.4 |
| 16 | 33.0 | 33.0 | 32.9 | 32.9 | 2 | 36.2 | 36.3 | 36.2 | 36.3 |
| 17 | 92.4 | 92.4 | 92.4 | 92.4 | 3 | 77.6 | 77.8 | 77.7 | 77.8 |
| 18 | 10.7 | 10.7 | 10.7 | 10.7 | 4 | 82.4 | 82.3 | 82.5 | 82.3 |
| 19 | 18.2 | 18.6 | 18.5 | 18.4 | 5 | 69.4 | 69.4 | 69.4 | 69.4 |
| 20 | 209.9 | 209.9 | 209.4 | 209.4 | 6 | 18.4 | 18.7 | 18.4 | 18.6 |
| 21 | 27.7 | 21.1 | 27.5 | 27.5 | OMe | 58.3 | 58.3 | 58.3 | 58.2 |
| | R2 substituent | | | | L-cym 1 | 98.9 | 99.0 | 98.9 | 99.0 |
| 1' | 165.8 | 165.8 | 165.9 | 166.0 | 2 | 32.3 | 32.1 | 32.4 | 32.1 |
| 2' | 119.2 | 119.2 | 114.1 | 114.1 | 3 | 73.3 | 76.4 | 73.3 | 76.4 |
| 3' | 145.0 | 145.0 | 165.5 | 165.5 | 4 | 78.8 | 73.2 | 78.8 | 73.3 |
| 4' | 135.0 | 135.0 | 38.1 | 38.1 | 5 | 65.2 | 66.4 | 65.2 | 66.4 |
| 5' | 128.6 | 128.6 | 20.8 | 20.8 | 6 | 18.2 | 18.2 | 18.2 | 18.1 |
| 6' | 129.3 | 129.3 | 20.9 | 20.9 | OMe | 56.8 | 56.6 | 56.8 | 56.6 |
| 7' | 130.6 | 130.6 | 16.4 | 16.4 | D-glc 1 | 102.3 | | 102.3 | |
| 8' | 129.3 | 129.3 | | | 2 | 75.3 | | 75.3 | |
| 9' | 128.6 | 128.6 | | | 3 | 78.7 | | 78.7 | |
| | | | | | 4 | 71.7 | | 71.7 | |
| | | | | | 5 | 78.4 | | 78.4 | |
| | | | | | 6 | 62.9 | | 62.9 | |

Notes:

D-cym: D-cymarose; L-dig: L-diginose; L-cym: L-cymarose; D-glc: D-glucose.

The invention claimed is:

1. A method of losing body weight, controlling body weight and inhibiting appetite of human beings or animals, comprising administering to the human beings or animals an effective amount of 3,8,12,14,17,20-oxo-substituted pregnene glycosides having the following formula I,

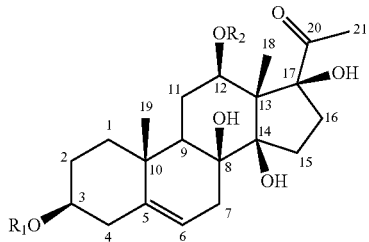

I wherein, $R_1$ is a saccharide group, and $R_2$ is an acyl group.

2. The method according to claim 1, wherein, in formula I, the saccharide group is selected from the group consisting of one or more sugar moieties selected from glucose, cymarose, diginose, mannose, xylose, rhamnose, arabinose, and glucuronic acid; and the acyl group is selected from acetyl, cinnamoyl, 3,4-dimethyl-2-amylene acyl, nicotinoyl, and benzoyl.

3. The method according to claim 1, wherein, 3,8,12,14, 17,20-oxo-substituted pregnene glycosides of formula I is selected from the group consisting of the following cynauricuoside A, wilfoside C1G, wilfoside K1N and wilfoside C1N:

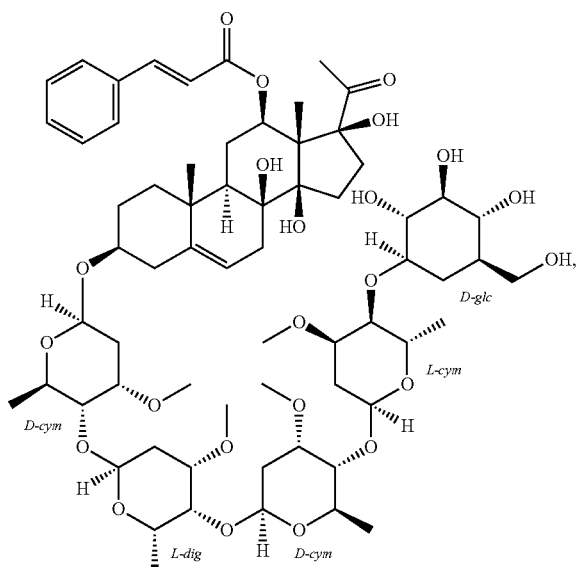
cynauricuoside A
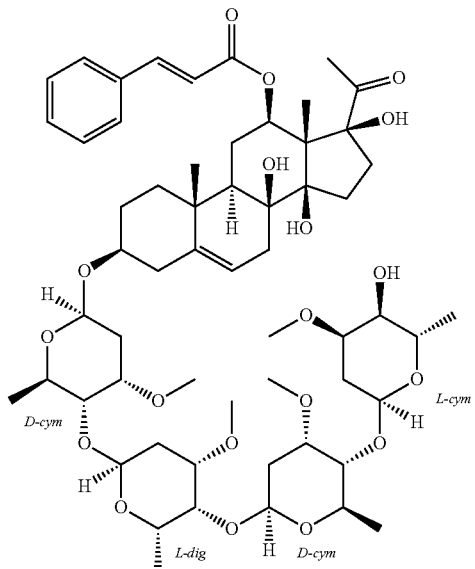
wilfoside K1N
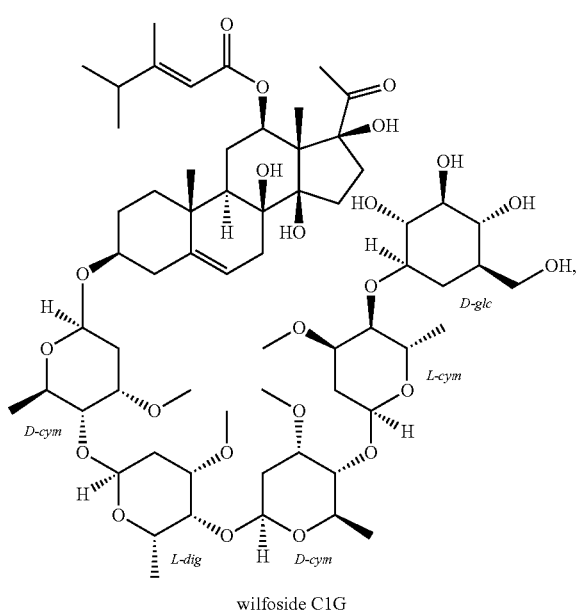
wilfoside C1G
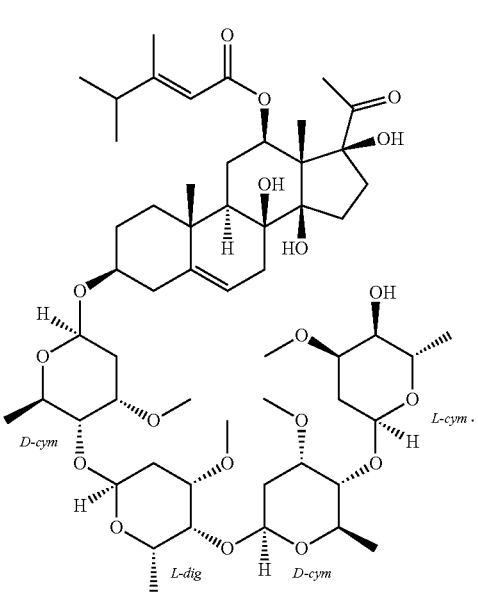
wilfoside C1N
4. The method according to claim 2, wherein, 3,8,12,14, 17,20-oxo-substituted pregnene glycosides of formula I is selected from the group consisting of the following cynauricuoside A, wilfoside C1G, wilfoside K1N and wilfoside C1N:

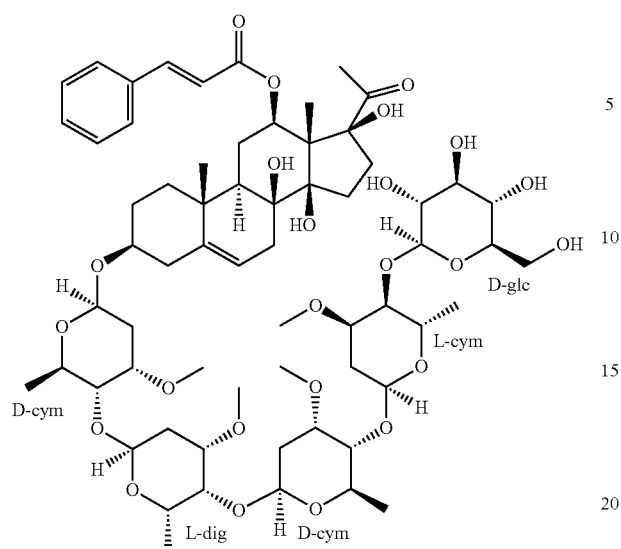
cynauricuoside A,
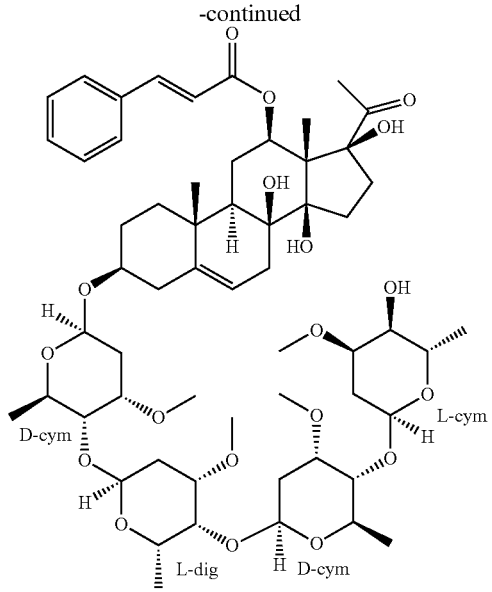
wilfoside K1N
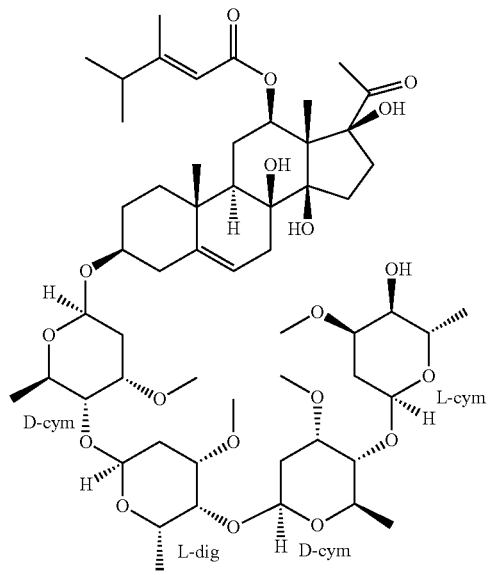
wilfoside C1G,
wilfoside C1N.
* * * * *